US012800586B2

(12) United States Patent
Schlaudraff

(10) Patent No.: US 12,800,586 B2
(45) Date of Patent: Nov. 17, 2026

(54) METHOD FOR GENERATING A MARKER IN A BIOLOGICAL SAMPLE

(71) Applicant: Leica Microsystems CMS GmbH, Wetzlar (DE)

(72) Inventor: Falk Schlaudraff, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 1055 days.

(21) Appl. No.: 17/959,315

(22) Filed: Oct. 4, 2022

(65) Prior Publication Data

US 2023/0105306 A1 Apr. 6, 2023

(30) Foreign Application Priority Data

Oct. 5, 2021 (EP) .................................... 21200842

(51) Int. Cl.

*G01N 33/58* (2006.01)
*C12N 15/63* (2006.01)
*C12Q 1/6806* (2018.01)

(52) U.S. Cl.

CPC ......... *G01N 33/582* (2013.01); *C12N 15/635* (2013.01); *C12Q 1/6806* (2013.01); *C12N 2830/002* (2013.01)

(58) Field of Classification Search

CPC ... G01N 33/582; G01N 33/533; C12Q 1/6806
See application file for complete search history.

(56) References Cited

U.S. PATENT DOCUMENTS 6,017,758 A 1/2000 Haselton, III et al.
2022/0090007 A1* 3/2022 Chien ................ G01N 21/6458

FOREIGN PATENT DOCUMENTS

EP 3686273 A1 7/2020
WO WO 2004/045547 A2 6/2004

OTHER PUBLICATIONS

Zhang et al. Photoregulation of protein plasmid expression in vitro and in vivo using BHQ caging group. Chinese Chemical Letters 22: 328-341 (2011).*

Hauke et al. Specific protein labeling with caged fluorophores for dual-color imaging and super-resolution microscopy in living cells. Chem Sci 8: 559-566 (2017).*

(Continued)

*Primary Examiner* — Gailene Gabel
(74) *Attorney, Agent, or Firm* — LEYDIG, VOIT & MAYER, LTD.

(57) ABSTRACT

A method generates a marker in a biological sample including a plurality of cells by means of oligonucleotide constructs. The method includes introducing at least a plurality of first oligonucleotide constructs into the biological sample. The plurality of first oligonucleotide constructs comprise a first promoter, a first nucleic acid sequence encoding a first fluorescent protein, and a first photoremovable cage molecule. The method also includes exposing, in particular scanning, at least a first region of the biological sample with a first spatially constrained light beam to form uncaged first oligonucleotide constructs in order to enable synthesis of first fluorescent proteins from the first nucleic acid sequence and generate at least a part of the marker in the first region of the biological sample.

14 Claims, 3 Drawing Sheets

(56) References Cited

OTHER PUBLICATIONS

Vorobev and Moskalensky, "Long-wavelength photoremovable protecting groups: On the way to in vivo application," Computational and Structural Biotechnology Journal, 18, Elsevier, Netherlands, Dec. 2020, pp. 27-34.
Zhi Ping Zhang et al.: "Photoregulation of protein plasmid expression in vitro and in vivo using BHQ caging group," Chinese Chemical Letters 22, Elsevier, Netherlands, pp. 338-341, Dec. 2011.
Monroe, W T et al: "Targeting expression with light using caged DNA," The Journal of Biological Chemistry, vol. 274, No. 30, pp. 20895-80900, Jul. 23, 1999, The American Society for Biochemistry and Molecular Biology, Inc., US.
Sebastian Hauke et al.: "Specific protein labeling with caged fluorophores for dual-color imaging and super-resolution microscopy in living cells," Chemical Science, Royal Society of Chemistry, UK, pp. 559-566, Dec. 2017.
Ellis-Davies, Graham C R: "Caged compounds: photorelease technology for control of cellular chemistry and physiology," Nature Methods, vol. 4 No. 8, Aug. 2007, pp. 619-628, Nature Publishing Group, UK.

* cited by examiner

METHOD FOR GENERATING A MARKER IN A BIOLOGICAL SAMPLE

CROSS REFERENCE TO RELATED APPLICATIONS

This application claims benefit to European Patent Application No. EP 21200842.9, filed on Oct. 5, 2021, which is hereby incorporated by reference herein.

FIELD

The invention relates to a method for generating a marker in a biological sample by means of oligonucleotide constructs. In further aspects the invention relates to an oligonucleotide construct and a system for generating a marker in a biological sample.

BACKGROUND

Recent progress in the fields of cell culture research has led to the advent of 3D cell culture, which is based on cultivating cells in three dimensions, for example, in suspension culture (scaffold-free techniques) or embedded in hydrogels and/or extracellular matrices (scaffold-based techniques). Further, cultivation of a plurality of cell clusters such as spheroids is enabled by these techniques. It is often desirable to frequently analyse, in particular individually image, these cell clusters in order to track growth or viability, for example. These cell clusters may be individually imaged for analysis, for example, in a flow cell.

However, when culturing these cell clusters in suspension, (visually) identifying or repeatedly recognising specific cell clusters is difficult for a large plurality of cell clusters. This is especially the case for large numbers of uniform cell clusters, such as spheroids. Thus, it remains difficult to keep track of specific cell clusters within a plurality of cell clusters, especially when iteratively imaging these cell clusters over several time points.

SUMMARY

In an embodiment, the present disclosure provides a method for generating a marker in a biological sample including a plurality of cells by means of oligonucleotide constructs. The method includes introducing at least a plurality of first oligonucleotide constructs into the biological sample. The plurality of first oligonucleotide constructs comprise a first promoter, a first nucleic acid sequence encoding a first fluorescent protein, and a first photoremovable cage molecule. The method also includes exposing, in particular scanning, at least a first region of the biological sample with a first spatially constrained light beam to form uncaged first oligonucleotide constructs in order to enable synthesis of first fluorescent proteins from the first nucleic acid sequence and generate at least a part of the marker in the first region of the biological sample.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
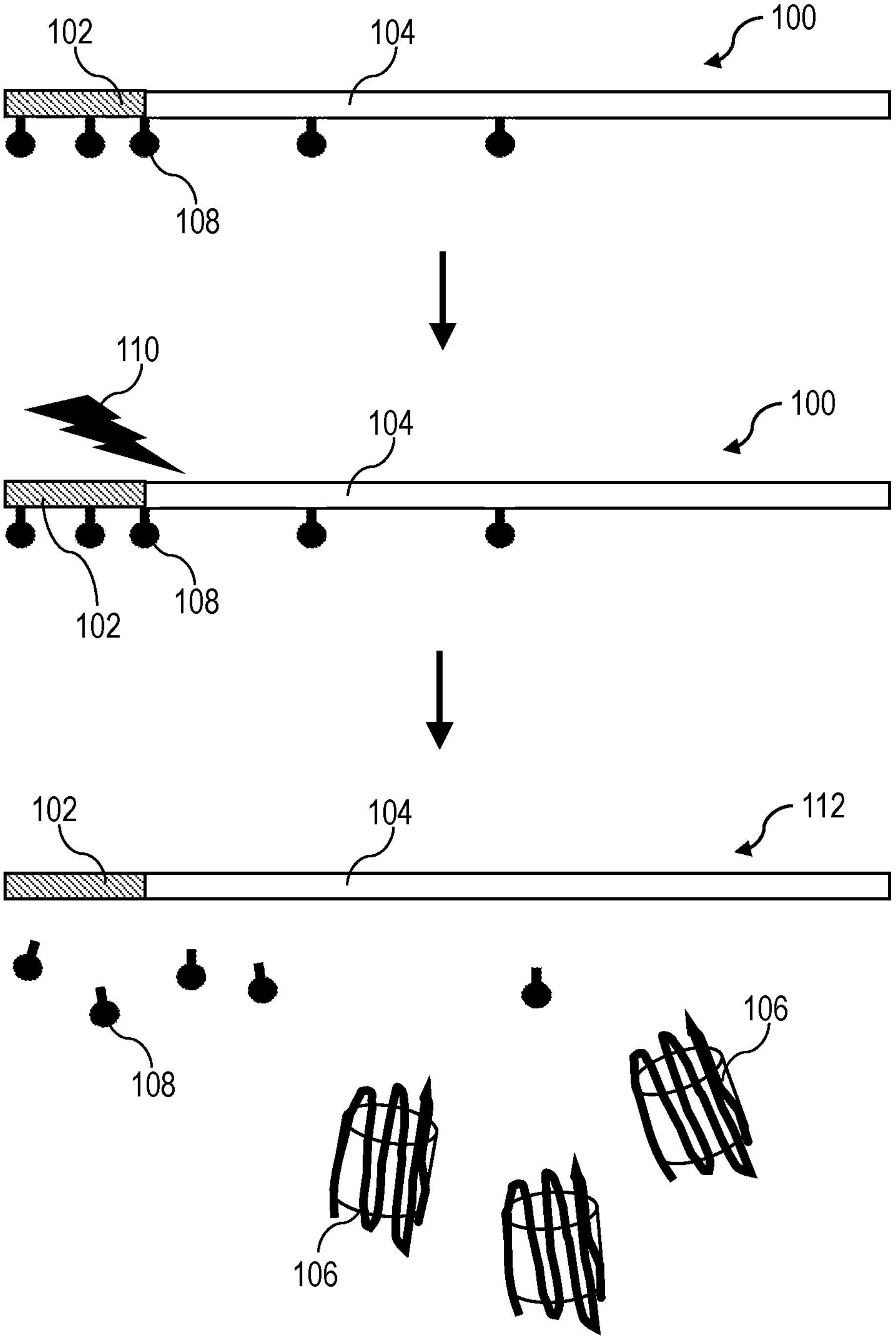
FIG. 1 shows a schematic view of an oligonucleotide construct for generating a marker in a biological sample.

Embodiments of the present invention provide a method, an oligonucleotide construct and a system for generating a marker in a biological sample, which enable uniquely labelling the biological sample, in particularly, to subsequently identify the biological sample.

In a first aspect a method is provided for generating a marker in a biological sample comprising a plurality of cells by means of oligonucleotide constructs. The method comprises the following steps: introducing at least a plurality of first oligonucleotide constructs into the biological sample, wherein the first oligonucleotide constructs comprise a first promoter, a first nucleic acid sequence encoding a first fluorescent protein, and a first photoremovable cage molecule; and exposing, in particular scanning, at least a first region of the biological sample with a first spatially constrained, in particular focused, light beam to form uncaged first oligonucleotide constructs in order to enable synthesis of first fluorescent proteins from the first nucleic acid sequence and generate at least a part of the marker in the first region of the biological sample. The biological sample may be in the form of a spheroid and, in particular, comprise living cells. In other words, the uncaging of the oligonucleotide constructs enables expression of the nucleic acid sequence and generation of the fluorescent protein in the cell or cells of the biological sample within the first region. This enables generating a marker in form of at least the first region in order to identify the marked biological sample based on the particular marker.

Certain embodiments prefer that the biological sample is imaged prior to the exposing step in order to generate an image of the biological sample, in particular to identify at least the first region in the image data, and/or wherein the biological sample is imaged after the exposing step in order to generate an image of the biological sample with the marker. By imaging the biological sample prior to generating the marker a suitable area for the region of the biological sample can be identified in the image. Further, coordinates of the region may be determined based on the position of the biological sample relative to an optical device configured to image the biological sample, enabling exposure of the region with high accuracy. In addition, the image of the biological sample prior to the exposure step may act as a baseline to compare further images to. In case images are taken after the exposure step, these images may be used to check successful generation of the marker. Further, these images after the exposure step may be compared to the baseline image.

Certain embodiments prefer that the step of introducing the oligonucleotide constructs is performed by transfection, in particular by lipofection or electroporation. This enables particularly efficient introduction of the oligonucleotide constructs into the biological sample.

In a preferred embodiment, a plurality of second oligonucleotide constructs is introduced into the biological sample, wherein the second oligonucleotide constructs comprise a second promoter, a second nucleic acid sequence encoding a second fluorescent protein, and a second photoremovable cage molecule. This enables generating a large number of distinguishable and unique markers.

In a particularly preferred embodiment, a second region of the biological sample is exposed with a second spatially constrained, in particular focused, light beam to form uncaged second oligonucleotide constructs in order to enable synthesis of second fluorescent proteins from the second nucleic acid sequence and generate at least a part of the marker in the second region of the biological sample. This enables the selective uncaging of the first and the second oligonucleotide constructs.

It is particularly preferred, that the first spatially constrained light beam and the second spatially constrained light beam differ in at least one light parameter, wherein said at least one light parameter comprises an uncaging wavelength, a predetermined pulse length or a light intensity. This enables the selective uncaging of the first and the second oligonucleotide constructs.

In a preferred embodiment, the first fluorescent protein and the second fluorescent protein have different fluorescent emission wavelengths. This enables optically distinguishing between the first regions and the second regions.

In a preferred embodiment, the spatially constrained light beams are generated by means of an optical device, in particular, by a widefield fluorescence microscope, an epifluorescence microscope, a light-sheet microscope, a confocal microscope, or a multiphoton microscope. The optical device may further be used for imaging the biological sample, for example, in a flow cell. This enables exposing the regions of the biological sample with the light beams with high precision and thus generate the marker with high precision.

In a preferred embodiment, the regions of the biological sample have one of the following shapes: circular, ovoid, linear, polygon, number, letter, a linear or curved dashed and/or point like structure (comparable to a Morse code), or the shape of a single cell of the biological sample. Such shapes or structures may be generated by a scanning microscope which is adapted to, for example, scan a spatially constrained—in particular a focused—light distribution along a two- or three-dimensional path that generates such a shape or structure. This enables generating a larger number of unique regions.

In a further aspect, an oligonucleotide construct is provided for generating a marker in a biological sample, in particular cellular samples. The oligonucleotide construct comprises a promoter, a nucleic acid sequence encoding a fluorescent protein, and at least one photoremovable cage molecule, photoremovable from the oligonucleotide construct by a spatially constrained, in particular focused, light beam. The removing of the cage molecule and thus generation of an uncaged oligonucleotide construct enables expression of the nucleic acid sequence and thus generation of the fluorescent protein.

Preferably, the oligonucleotide construct comprises RNA nucleotides, DNA nucleotides and/or locked nucleic acid (LNA) nucleotides. This enables flexible manufacture of the oligonucleotide construct.

In a preferred embodiment the oligonucleotide construct is linear or circular. This enables varying the half-life of the oligonucleotide construct, with circular oligonucleotides generally being more stable and having a longer half-life.

In a preferred embodiment the photoremovable cage molecules are attached to the promoter. This enables particularly effective caging of the oligonucleotide construct.

In a further aspect, a system is provided for generating a marker in a biological sample, in particular cellular samples. The system comprises: at least one first oligonucleotide construct comprising a first promoter, a first nucleic acid sequence encoding a first fluorescent protein, and a first photoremovable cage molecule; wherein the first photoremovable cage molecule is photoremovable from the first oligonucleotide construct by a first spatially constrained, in particular focused, light beam; and an optical device configured to provide a first spatially constrained light beam and to generate the marker in the biological sample. The selective removal of the first cage molecule and thus selective generation of a respective uncaged oligonucleotide construct enables selective expression of the respective nucleic acid sequence and thus generation of the corresponding fluorescent protein only in areas exposed to corresponding light beam. Further, markers may be generated by the system in more than the one biological sample.

In a preferred embodiment the system further comprises at least one second oligonucleotide construct comprising a second promoter, a second nucleic acid sequence encoding a second fluorescent protein, and a second photoremovable cage molecule; wherein the second photoremovable cage molecule is photoremovable from the second oligonucleotide construct by a second spatially constrained, in particular focused, light beam, and wherein the optical device is further configured to provide a second spatially constrained light beam to generate the marker in the biological sample. The selective removal of the first and second cage molecules and thus selective generation of uncaged oligonucleotide constructs enables selective expression of the respective nucleic acid sequence and thus generation of the corresponding fluorescent protein only in areas exposed to corresponding light beam.

In a particularly preferred embodiment, the optical device is configured to expose at least a first region of the biological sample to the first light beam and at least a second region of the biological sample to the second light beam. The light beams uncage the respective oligonucleotide constructs in order to enable synthesis of the corresponding fluorescent proteins and generate at least a part of the marker in the respective region of the biological sample.

In a preferred embodiment, the first fluorescent protein and the second fluorescent protein have different fluorescent emission wavelengths. This enables optically distinguishing between the first regions and the second regions.

Preferably, the first spatially constrained light beam and the second spatially constrained light beam differ in at least one light parameter, wherein said at least one light parameter comprises an uncaging wavelength, a predetermined pulse length, or a light intensity. This enables the selective uncaging of the first and the second oligonucleotide constructs.

In a preferred embodiment the first promoter and the second promoter have the same nucleotide sequence, or the first promoter and the second promoter have different nucleotide sequences. This enables matching the promoter activity to the fluorescence emission intensity of the respective fluorescent protein.

FIG. 1 shows an example of an oligonucleotide construct 100 for generating a marker in a biological sample. The oligonucleotide construct 100 is a single stranded, or alternatively double stranded, deoxyribonucleic acid (DNA) molecule comprising a promoter region 102 and a fluorescent protein region 104. The fluorescent protein region 104 is a nucleic acid sequence that encodes a first fluorescent protein 106. The promoter 102 is a nucleic acid sequence that acts as the starting point for transcription and/or translation, in order to synthesise the fluorescent protein 106 from the fluorescent protein region 104. The promoter is at a 5' end of the oligonucleotides construct 100. The construct 100 may additionally or alternatively be a ribonucleic acid (RNA) and/or a locked nucleic acid (LNA).

The oligonucleotide construct 100 further comprises at least one photoremovable cage molecule 108, preferably bound to the promoter region 102. The photoremovable cage molecule 108 is a photolabile protecting group and cleavable from the oligonucleotide construct 100 by light 110 at a predetermined wavelength. In particular, the cage molecule 108 may be covalently bound to a nucleobase of the promoter region 102, with the light 110 causing the covalent bond to break and release the cage molecule. The bound cage molecule 108 prevents, for example, the binding of enzymes to the promoter region 102. This prevents transcription and/or translation of the oligonucleotide construct 100, and therefore the synthesis of the fluorescent protein 106 from the fluorescent protein region 104. Regularly, the construct 100 comprises a plurality of cage molecules 108.

FIG. 1 further shows the cage molecules 108 removed from the oligonucleotide construct 100 to form an unprotected oligonucleotide construct 112. In the presence of suitable enzymes, such as polymerases and/or ribosomes, and additional elements such as nucleotides and/or transfer RNA molecules, the fluorescent protein 106 may be synthesised from the unprotected oligonucleotide construct 112.

Figure 2:
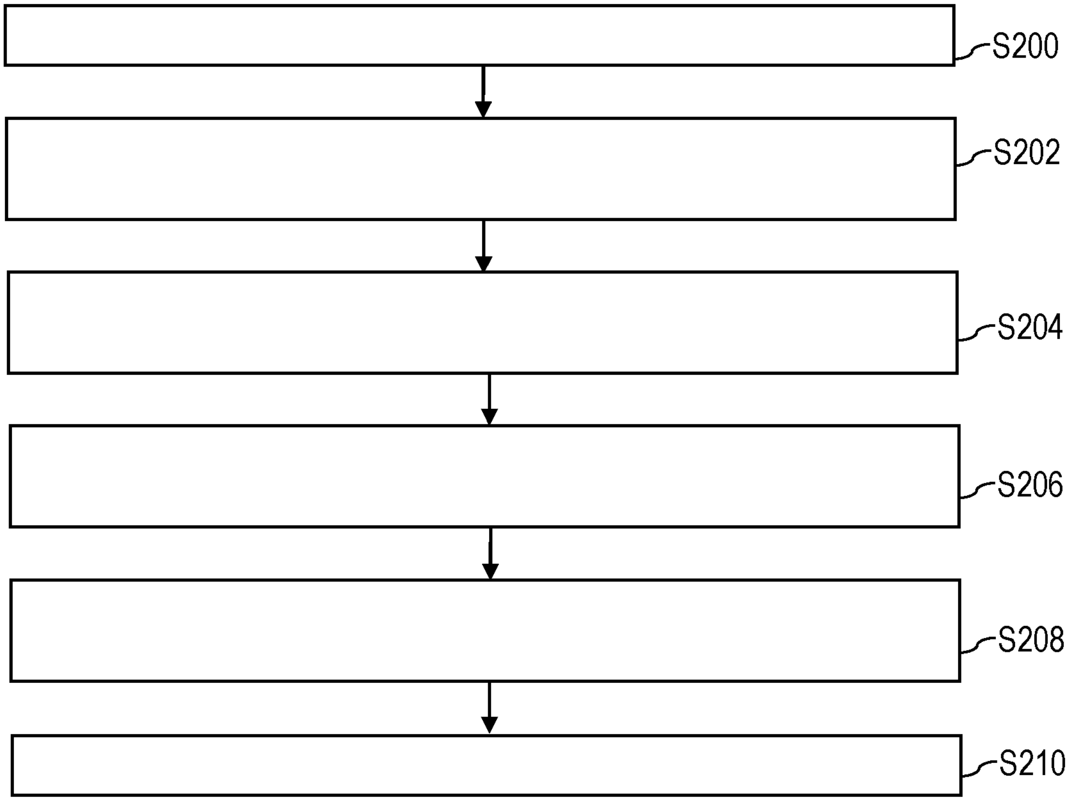
FIG. 2 shows a flow chart of a method for generating a marker in a biological sample.

FIG. 2 shows a flow chart of a method for generating a marker in a biological sample. In particular, the biological sample is one of a plurality of biological samples. The biological sample comprises a plurality of cells. In preferred embodiments the cells are viable cells, in particular, mammalian cells. For example, the biological sample may be a spheroid.

The method starts in step S200. In step S202, the biological sample or the plurality of biological samples is incubated in the presence of a plurality of at least the oligonucleotide constructs 100 in order to introduce the oligonucleotide constructs 100 into the biological sample. For example, this can be achieved by transfecting the cells of the biological sample with the oligonucleotide construct 100. Particularly suitable methods of transfection are lipofection and electroporation. This results in the oligonucleotide constructs 100 being introduced into the cells of the biological sample, in particular into the cytoplasm of the cells.

In step S204, at least a first region of the biological sample is exposed to or scanned with a first spatially constrained light beam. The first spatially constrained light beam is configured to remove the photoremovable cage molecules 108 from the oligonucleotide construct 100, in particular, only from those oligonucleotide constructs 100 in the first region. For example, the first light beam may have a specific wavelength, which causes the photo-removal of the cage molecule 108. Alternatively or in addition, other parameters of the first light beam may cause the photo-removal of the cage molecule 108, for example, the light intensity or the length of time for which the region is exposed to the light beam. The spatially constrained light beam may be generated and directed by means of an optical device, in particular a fluorescence microscope, a light-sheet microscope, a confocal microscope, or a multiphoton microscope.

In addition, the biological sample may be imaged in step S204 before and/or after the first region is exposed to the first light beam. The image may be generated by the optical device, as well, for example, with a microscope comprising a flow cell. In particular, an image taken before exposing the first region to the first light beam may be used to identify the first region in the biological sample and generate coordinates that describe the position of the first region within the biological sample. The optical device may then expose the first region defined by the coordinates. Moreover, the biological sample may be imaged after exposing the first region with the first light beam.

Once the cage molecules 108 are removed from the oligonucleotides constructs 100 in the first region and respective oligonucleotide constructs 112 are generated, the fluorescent protein regions 104 of oligonucleotide constructs 112 within cells of the biological sample in the first region are expressed. This results in the fluorescent protein 106 being produced within cells of the first region of the biological sample. The first region with the fluorescent proteins 106 may also be called a marker, which marks or labels the biological sample.

In step S206 the biological sample is stored, for example in a liquid in a reservoir for the purpose of cultivation. Alternatively, the biological sample may be processed in experimental analysis or subjected to experimental conditions. During step S206, the biological sample may be stored in the reservoir together with other biological samples of the plurality of biological samples.

In step S208 the biological sample is imaged, for example, by means of the optical device. In addition, in case in step S206 the biological sample is stored in the reservoir together with other biological samples of the plurality of biological samples, each biological sample of the plurality of biological samples may be imaged. Further in step S208 it is determined whether or not the marker, in particular, the biological sample with the marker, is present in one of the images generated in step S208. This enables identifying or recognising the biological sample with the marker. Further, this enables comparing the image of the biological sample with images of the biological sample that were previously generated.

The method ends in step S210.

Alternatively to performing steps S206 and S208, the method may end in step S210 after step S204, and therefore only comprise the steps S200, S202, S204 and S210.

Moreover, the steps S206 and S208 may be iterated. Thus, the biological sample with the marker may be repeatedly stored or processed (S206) and subsequently imaged and identified (S208).

Alternatively, in step S204, at least a second region of the biological sample may be exposed to the first light beam. This results in a marker with the first region and the second region expressing the fluorescent protein regions 104 and generating the fluorescent protein 106. This enables generating a more diverse set of possible markers. For example, by varying the distance between the first and second region, several distinct and distinguishable, in particular, unique, markers may be generated. When generating these distinguishable markers in several separate biological samples, this further enables distinguishing between these several biological samples in step S208.

Additionally or alternatively, the plurality of biological samples may be incubated in step S202 with the plurality of oligonucleotide constructs 100 and a plurality of second oligonucleotide constructs in order to introduce the oligonucleotide constructs 100 and the second oligonucleotide constructs into the biological sample. The second oligonucleotide constructs differ from the oligonucleotide constructs 100 by comprising a second fluorescent protein region, which is a nucleic acid sequence encoding a second fluorescent protein, by comprising a second photoremovable cage molecule, and by comprising a second promoter. The fluorescent protein 106 differs from the second fluorescent protein by having different fluorescent properties such as fluorescent excitation wavelength, emission wavelength and/or emission intensity.

The cage molecule 108 and the second cage molecule differ in their conditions under which they are photoremovable from the respective oligonucleotide construct. Specifically, the cage molecule 108 and the second cage molecule may be removed from the respective oligonucleotide construct by light with differing parameters. These parameters include wavelength, intensity and duration of scanning. For example, the cage molecule 108 may be a protecting group removable by ultraviolet light such as 6-nitropiperonyloxymethyl. Whereas the second cage molecule may be a protecting group removable by a different wavelength, for example, near-infrared light, as described by Vorobev and Moskalensky (c.f. Vorobev A Y, Moskalensky A E. Long-wavelength photoremovable protecting groups: On the way to in vivo application. Computational and Structural Biotechnology Journal, 2020, 18, 27-34.). This enables selectively removing the cage molecules 108 or the second cage molecules from the respective plurality of oligonucleotide constructs. In addition, scanning with longer wavelength light, such as near-infrared light, results in less damage of the biological structures scanned by the light beam.

The promoter 102 and the second promoter may comprise the same sequence. Alternatively, the promoter 102 and the second promoter may have different sequences, in particular, the promoters may differ in case the respective oligonucleotide constructs have fluorescent protein regions, which express fluorescent proteins with differences in their respective fluorescence emission intensity, for example. In this case, the promoter activity of an oligonucleotide construct may be matched to the respective fluorescence emission intensity.

In a further embodiment, in the step S204, at least a second region of the biological sample is then exposed to or scanned with a second spatially constrained light beam. This second light beam is configured to remove the second photoremovable cage molecules from the second oligonucleotide construct, in particular, only from those second oligonucleotide constructs in the second region. As described above, the first and second light beams have different properties in order to selectively remove the cage molecules 108 or the second cage molecules. Thus, in the first region only the oligonucleotide constructs 108 are uncaged and in the second region only the second oligonucleotide constructs are uncaged. Consequently, in the first region only the first fluorescent proteins 106 are generated and in the second region only the second fluorescent proteins are generated. This enables generating an even more diverse set of possible markers. For example, by having regions of different fluorescent colours in addition to varying the distance between the regions, a large number of distinct and distinguishable markers may be generated. This enables distinguishing between a larger number of biological samples in step S208.

Figure 3:
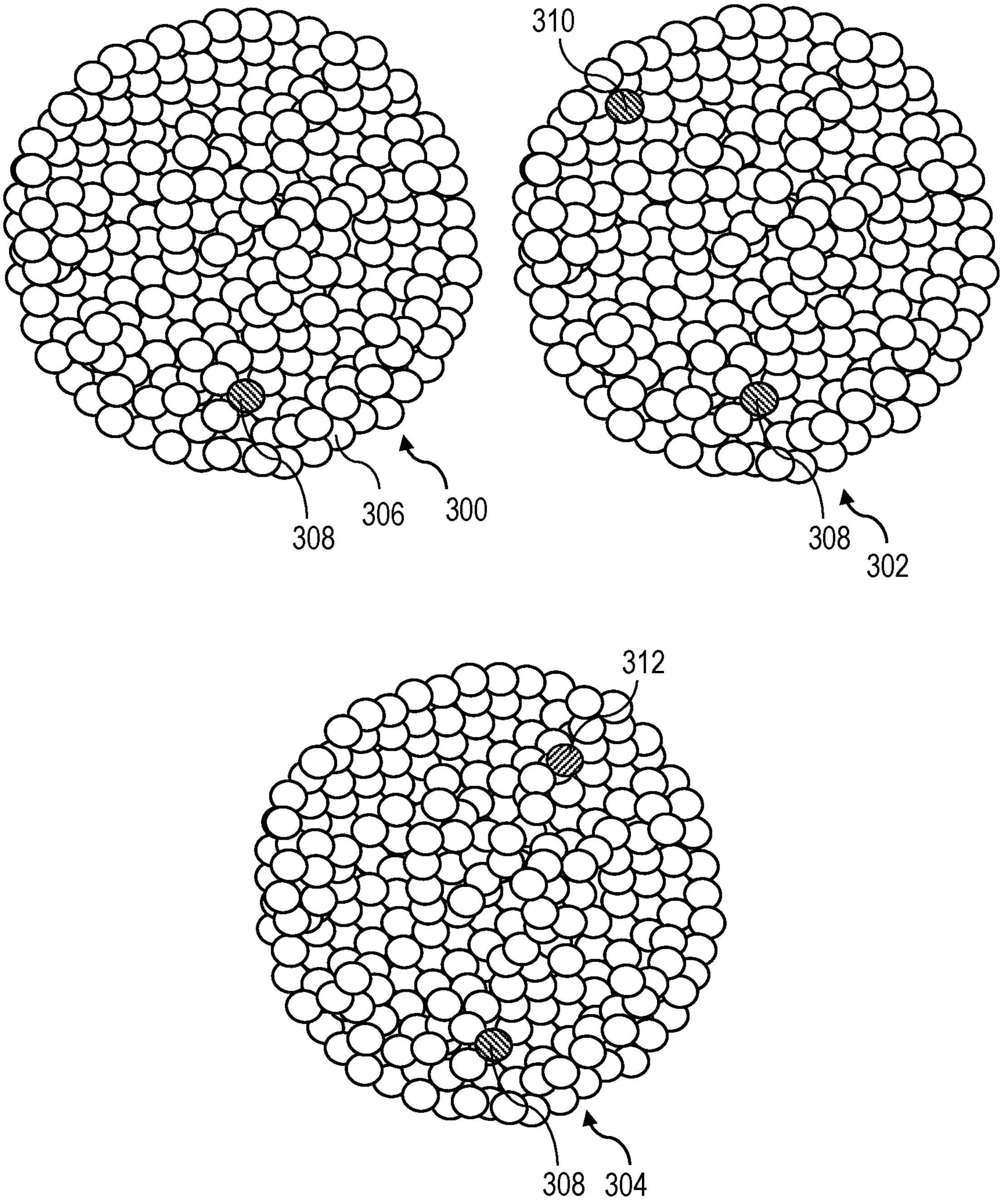
FIG. 3 shows three biological samples with markers.

FIG. 3 shows by way of example three biological samples 300, 302, 304, each with markers generated by the method described for FIG. 2. The biological samples 300, 302, 304 comprise a plurality of cells 306. The biological sample 300 has a marker that comprises a first fluorescent cell 308 generating the first fluorescent protein with a first emission wavelength. The biological sample 302 has a marker that comprises the first fluorescent cell 308 and a second fluorescent cell 310 similarly generating the first fluorescent protein. The biological sample 304 has a marker that comprises the first fluorescent cell 308 and a third fluorescent cell 312 generating the second fluorescent protein at a second emission wavelength.

As an example, the biological samples 300, 302, 304 shown in FIG. 3 may be stored in a reservoir together. The unique markers on each biological sample 300, 302, 304 would nevertheless enable identifying and/or distinguishing the biological samples 300, 302, 304 from each other.

For the biological sample 300, 302, 304, the regions exposed to the respective light beams were shaped in the form of the respective cells 308, 310, 312. Alternatively, the regions may form an oval shape, or a rectangular shape on the biological sample. Further, the regions may comprise several cells, such that several adjacent cells may generate the respective fluorescent protein.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

100 Oligonucleotide construct
102 Promoter region
104 Fluorescent protein region
106 Fluorescent protein
108 Photoremovable cage molecule
110 Light
112 Uncaged oligonucleotide construct
300, 302, 304 Biological sample with marker

306 Cell

308, 310, 312 Fluorescent cell

The invention claimed is:

1. A method for generating a marker in a biological sample by oligonucleotide constructs, the biological sample being a 3D cell culture and comprising a plurality of cells, the method comprising:

introducing a plurality of first oligonucleotide constructs into the biological sample, wherein the plurality of first oligonucleotide constructs comprises a first promoter, a first nucleic acid sequence encoding a first fluorescent protein, and a first photoremovable cage molecule, introducing a plurality of second oligonucleotide constructs into the biological sample, wherein the plurality of second oligonucleotide constructs comprises a second promoter, a second nucleic acid sequence encoding a second fluorescent protein, and a second photoremovable cage molecule, exposing a first region of the biological sample with a first spatially constrained light beam to form uncaged first oligonucleotide constructs in order to enable synthesis of first fluorescent proteins from the first nucleic acid sequence and generate at least a first part of the marker in the first region of the biological sample, and exposing a second region of the biological sample with a second spatially constrained light beam to form uncaged second oligonucleotide constructs in order to enable synthesis of second fluorescent proteins from the second nucleic acid sequence and generate a second part of the marker in the second region of the biological sample, wherein the first region of the biological sample contains a first cell of the plurality of cells, and the second region of the biological sample contains a second cell of the plurality of cells spaced at a distance from the first cell.

2. The method according to claim 1, wherein the biological sample is imaged prior to the exposing the first region and the exposing the second region in order to generate an image of the biological sample, and/or wherein the biological sample is imaged after the exposing the first region and the exposing the second region in order to generate an image of the biological sample with the marker.

3. The method according to claim 1, wherein the introducing the plurality of first oligonucleotide constructs and the introducing the plurality of second oligonucleotide constructs are performed by transfection.

4. The method according to claim 1, wherein the first spatially constrained light beam and the second spatially constrained light beam differ in at least one light parameter, wherein the at least one light parameter comprises an uncaging wavelength, a predetermined pulse length, or a light intensity.

5. The method according to claim 1, wherein the first fluorescent protein and the second fluorescent protein have different fluorescent emission wavelengths.

6. The method according to claim 1, wherein the first spatially constrained light beam and the second spatially constrained light beam are generated by an optical device including at least one of a widefield fluorescence microscope, an epi-fluorescence microscope, a light-sheet microscope, a confocal microscope, or a multiphoton microscope.

7. The method according to claim 1, wherein the first region and the second region of the biological sample have one of a following shape: circular, ovoid, linear, or a shape of the first cell or the second cell of the biological sample.

8. The method according to claim 1, wherein the exposing the first region and the exposing the second region comprise scanning the first region and scanning the second region.

9. The method according to claim 1, wherein the first spatially constrained light beam is a first focused light beam, and the second spatially constrained light beam is a second focused light beam.

10. A system for generating a marker in a biological sample, the biological sample being a 3D cell culture and comprising a plurality of cells, the system comprising:

at least one first oligonucleotide construct comprising a first promoter, a first nucleic acid sequence encoding a first fluorescent protein, and a first photoremovable cage molecule, wherein the first photoremovable cage molecule is photoremovable from the first oligonucleotide construct by a first spatially constrained light beam, at least one second oligonucleotide construct comprising a second promoter, a second nucleic acid sequence encoding a second fluorescent protein, and a second photoremovable cage molecule, wherein the second photoremovable cage molecule is photoremovable from the second oligonucleotide construct by a second spatially constrained light beam, an optical device configured to:

provide the first spatially constrained light beam to expose a first region of the biological sample to form uncaged first oligonucleotide constructs in order to enable synthesis of first fluorescent proteins from the first nucleic acid sequence and to generate a first part of the marker in the biological sample, and provide the second spatially constrained light beam to expose a second region of the biological sample to form uncaged second oligonucleotide constructs in order to enable synthesis of second fluorescent proteins from the second nucleic acid sequence and to generate a second part of the marker in the biological sample, wherein the first region of the biological sample contains a first cell of the plurality of cells, and the second region of the biological sample contains a second cell of the plurality of cells spaced at a distance from the first cell.

11. The system according to claim 10, wherein the first fluorescent protein and the second fluorescent protein have different fluorescent emission wavelengths.

12. The system according to claim 10, wherein the first spatially constrained light beam and the second spatially constrained light beam differ in at least one light parameter, wherein the at least one light parameter comprises an uncaging wavelength, a predetermined pulse length, or a light intensity.

13. The system according to claim 10, wherein the first promoter and the second promoter have a same nucleotide sequence, or wherein the first promoter and the second promoter have different nucleotide sequences.

14. The system according to claim 10, wherein the first spatially constrained light beam is a focused light beam, and the second spatially constrained light beam is a second focused light beam.

* * * * *